United States Patent [19]

Czarniecki et al.

[11] Patent Number: 4,766,109

[45] Date of Patent: Aug. 23, 1988

[54] HYDROPHOBIC PEPTIDES

[75] Inventors: Michael F. Czarniecki, Westfield; Laura L. Verbiar, Verona; Timothy Kogan, Union, all of N.J.

[73] Assignee: Schering Corporation, Kenilworth, N.J.

[21] Appl. No.: 919,950

[22] Filed: Oct. 17, 1986

[51] Int. Cl.[4] .......................... A61K 37/02; C07K 7/06
[52] U.S. Cl. ....................................... 514/17; 530/330
[58] Field of Search ........................... 530/330; 514/17

[56] References Cited

U.S. PATENT DOCUMENTS 4,629,724 12/1986 Ryono et al. ...................... 530/330

*Primary Examiner*—Delbert R. Phillips
*Assistant Examiner*—Christina Chan
*Attorney, Agent, or Firm*—Anita W. Magatti; Stephen I. Miller; Gerald S. Rosen

[57] ABSTRACT

Hydrophobic peptides having antihypertensive activity are disclosed. Also disclosed are pharmaceutical compositions comprising a hydrophobic peptide and a method of treatment of mammalian hypertension comprising administering a hydrophobic peptide to a hypertensive mammal.

16 Claims, No Drawings

HYDROPHOBIC PEPTIDES

SUMMARY OF THE INVENTION

The present invention relates to hydrophobic peptides which have antihypertensive activity.

The invention also relates to pharmaceutical compositions comprising the hydrophobic peptides of this invention, and to a method of treatment of hypertension comprising administering a hydrophobic peptide of this invention to a hypertensive mammal.

DESCRIPTION OF THE INVENTION

The hydrophobic peptides of the present invention are represented by the following formula:

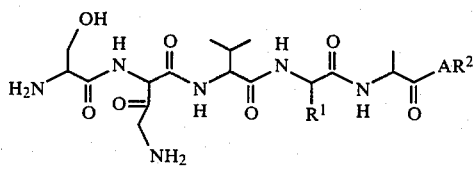

wherein
A is —O— or —NH—;
$R^1$ is arylmethyl; substituted arylmethyl wherein the substituents on the aryl croup are 1–3 substituents selected from hydroxy, halogen, lower alkyl, lower alkoxy, cycloalkyl or aryl; cycloalkylmethyl; substituted cycloalkylmethyl wherein the substituents are as defined for arylmethyl; heteroarylmethyl; or substituted heteroarylmethyl wherein the substituents are as defined for arylmethyl;
$R^2$ is arylmethyl; cycloalkylmethyl; substituted arylmethyl or substituted cycloalkylmethyl, wherein the substituents are as defined above for arylmethyl; and the pharmaceutically acceptable salts thereof.

As used herein the term "aryl" means phenyl; a bi- or polycyclic phenyl fused ring system having 10–14 carbon atoms; or a bi- or polycyclic phenyl ring system wherein two or more phenyl rings are bonded to each other by ring carbons or two or more phenyl rings are bonded to an alkyl group. Examples of aryl groups are phenyl, naphthyl, anthracenyl, phenanthrenyl, fluorenyl, biphenyl and diphenylmethyl. All positional isomers are contemplated, e.g. 9-anthracehyl, 1-naphthyl and 2-naphthyl.

"Cycloalkyl" means cyclic alkyl groups of 3–7 carbon atoms. Lower alkyl refers to straight or branched chain alkyl croups of 1 to 6 carbon atoms, and lower alkoxy similarly refers to alkoxy groups having from 1 to 6 carbon atoms.

"Heteroaryl" means a monocyclic or bicyclic fused ring system comprising 5–10 atoms wherein 1 or more ring atoms are independently selected from nitrogen, oxygen or sulfur and the remaining ring atoms are carbon. Examples of heteroaryl groups are pyrrolyl, furyl, pyrazolyl, thiophenyl, pyranyl, pyridyl, pyrimidyl, pyrizinyl, thiopyranyl and their benzo fused analogs.

"Halogen" means chlorine, bromine or iodine radicals.

A preferred embodiment of the present invention comprises compounds of formula I wherein the aryl portion of $R^1$ is a mono- or dihalogenated phenol, e.g. $R^1$ is

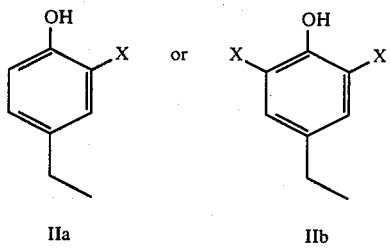

IIa IIb wherein X is halogen. Compounds wherein the aryl portion of $R^1$ is a mono- or di-iodo phenol are more preferred.

Another preferred embodiment of the invention comprises compounds of formula I wherein A is —O—.

A third preferred embodiment of compounds of formula I comprises compounds wherein $R^2$ is benzyl.

More preferred are compounds of formula I wherein A is —O—, $R^2$ is benzyl and wherein the aryl portion of $R^1$ is mono- or dihaloqenated phenol Compounds of this invention form salts with various inorganic and organic acids and bases. Such salts include salts prepared with organic and inorganic acids, e.g. HCl, HBr, $H_2SO_4$, $H_3PO_4$, methanesulfonic acid, toluenesulfonic acid, maleic acid, furmaric acid and camphorsulfonic acid. Salts prepared with bases include ammonium salts, alkali metal salts, e.g. sodium and potassium salts, and alkaline earth salts, e.g. calcium and magnesium salts. Hydrochloride salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of the instant invention include various stereoisomers as indicated in the following formula wherein chiral centers are marked with an asterisk:

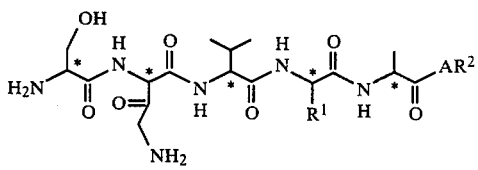

and wherein $R^1$, $R^2$ and A are as defined above. In the preferred compounds of this invention, the chiral centers on the peptide "backbone", i.e. the peptide molecule without $R^1$ and $R^2$, are either all R or all S.

Compounds of the present invention may be prepared by using coupling reactions well known in the peptide art. The following reaction scheme is a general example:

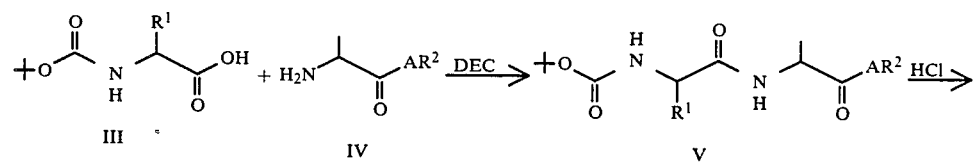
III + IV → V
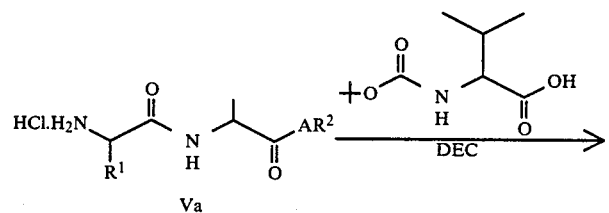
Va
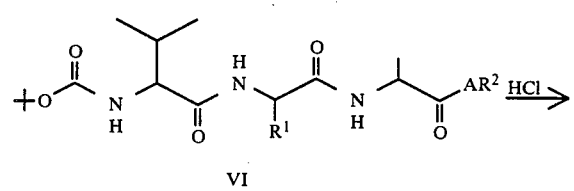
VI
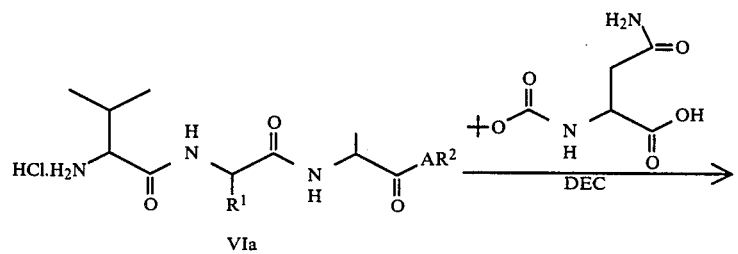
VIa
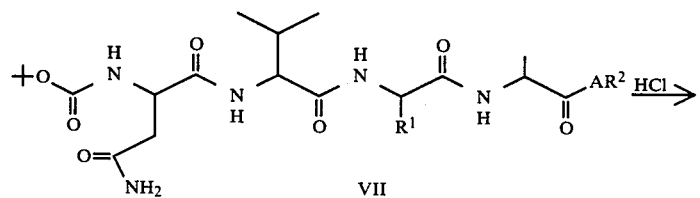
VII
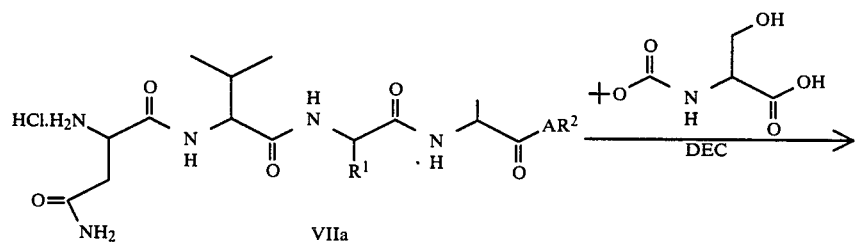
VIIa
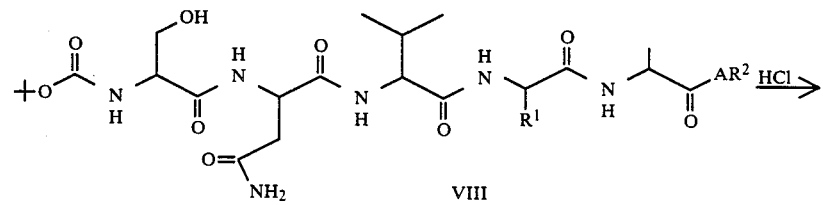
VIII -continued

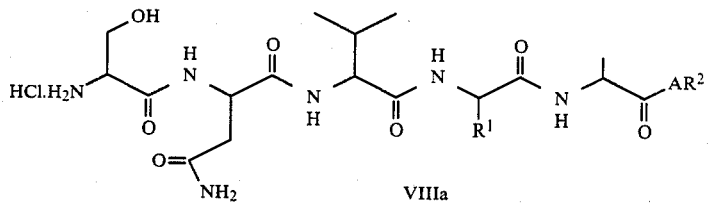

As can be seen by reference to the above scheme, the peptides of the invention are prepared by successively adding on the desired amino acid fragments. Typically, an α-N-carbamoyl protected amino acid and a carboxyl-protected amino acid are reacted at room temperature in an inert solvent such as dimethylformamide in the presence of coupling agents such as 1-(3-dimethylaminopropyl)-3-ethyl carbodiimide and 1-hydroxybenzotriazole in the presence of a base such as N-methylmorpholine. The α-N-carbamoyl protecting group is removed from the resultant peptide, and the coupling reaction repeated with the next desired N-protected amino acid. Suitable N-protecting groups are well known in the art, with t-butyloxycarbonyl herein preferred.

The starting hydrophobic amino acids of formula III are also prepared by well-known methods. For example, a malonic ester-type synthesis reacting $R^1$-halides (preferably $R^1$-Br) with diethyl acetamidomalonate followed by hydrolysis may be used to prepare the $R^1$-containing amino acid, which may then be N-protected by conventional means. Starting compounds of formula X ($R^1$-Br) are readily available by known methods. A schematic example of such syntheses follows:

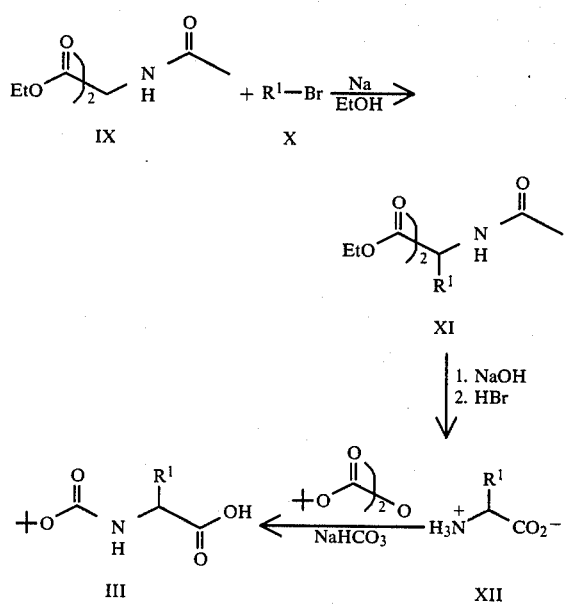

Following are examples of the preparation of compounds of the present invention.

EXAMPLE 1

Seryl-Asparaginyl-Valyl-(3,3Diphenyl)Alanyl-alanine Benzyl Ester, Hydrochloride

A. Diethyl 2-Acetamido-2-(Diphenylmethyl)Malonate

Dissolve sodium (2 g) in 400 ml ethanol and add diethyl acetamidomalonate (10.4 g). Stir 5 minutes, add diphenyl bromomethane (12.4 g), and stir 7 hours at room temperature. Acidify the reaction mixture, partition between water and methylene chloride ($CH_2Cl_2$), dry the organic layer over magnesium sulfate ($MgSO_4$), filter, and evaporate the solvent to obtain the crude title compound as a pale yellow oil. $R_f$ (silica gel; $Et_2O$)=0.89.

B. 3,3-Diphenylalanine

Dissolve the product prepared in Part A in 300 ml 48% hydrobromic acid and reflux for 12 hours. Evaporate the acid under reduced pressure and dissolve the residue in water. Neutralize the solution with 1N sodium hydroxide (NaOH) and apply to a column of Dowex-50 ($H^+$) (30×4.6 cm). Wash the column with 100 ml water and elute the product with 150 ml 1N ammonium hydroxide. Evaporate the eluent to dryness to give the title compound. $R_f$ (silica gel; $CHCl_3$:$CH_3OH$:32% aqueous $CH_3CO_2H$, 6:3:1)=0.73.

C. N-α-t-Butyloxycarbonyl-(3,3-Diphenyl)Alanine

Suspend the product prepared in Part B (2 g) in 20 ml dioxane:$H_2O$, 2:1, add 7 ml 1N NaOH and cool the mixture to 0° C. Add di-tert-butyl carbonate (2 g) dropwise and stir several hours, allowinq the reaction to come to room temperature. Extract with petroleum ether, concentrate the acueous layer and acidify to pH 3.0 with solid potassium bisulfate ($KHSO_4$). Extract the product from the water with $CH_2Cl_2$ and evaporate the solvent to obtain the title compound. $R_f$ (silica gel; $CH_2Cl_2$:$CH_3OH$, 9:1)=0.61.

D. N-α-t-Butyloxycarbonyl-(3,3-Diphenyl)Alanyl-Alanine Benzyl Ester

Combine the product of Part C (.47 g), alanine benzyl ester hydrochloride (0.29 g), 1-(3-dimethylaminopropyl)-3-ethylcarbodiimide hydrochloride (DEC) (0.26 g), 1-hydroxybenzotriazole hydrate (.21 g), and N-methylmorpholine (0.14 g) in 3 ml anhydrous dimethylformamide (DMF). Stir 12 hours and evaporate the solvent. Suspend the residue in ethylacetate (EtOAc) and wash successively with saturated aqueous sodium bicarbonate ($NaHCO_3$), 10% citric acid, and water. Dry the organic layer over $MgSO_4$, filter, and evaporate the solvent to give the title compound. $R_f$ (silica gel; $CH_2Cl_2$:$CH_3OH$, 97.5:2.5)=0.84.

E. N-α-t-Butyloxycarbonyl-Valyl-(3,3-Diphenyl)Alanyl-Alanine Benzyl Ester

Add 6M HCl in dioxane (10 ml) to the product of Part D (0.5 g), stir 10 minutes and evaporate the solvent. Add N-α-t-butyloxycarbonyl-valine (0.22 g), DEC (0.019 g), 1-hydroxybenzotriazole (0.15 g), N-methylmorpholine (0.1 g) and anhydrous DMF (2 ml) to the residue. Stir 12 hours and evaporate the solvent. Suspend the residue in EtOAc and wash successively with saturated acueous NaHCO$_3$, 10% citric acid, and water. Dry the organic layer over MgSO$_4$, filter, and evaporate the solvent to obtain the title compound. R$_f$(silica gel; CH$_2$Cl$_2$:CH$_3$OH, 95:5)=0.87.

F. N-α-t-Butyloxycarbonyl-Asparaginyl-Valyl-(3,3-Diphenyl)Alanyl-Alanine Benzyl Ester Add 6M HCl in dioxane (10 ml) to the product of Part E (.6 g). Stir 10 minutes and evaporate excess acid and solvent. Add to this residue N-α-t-butyloxycarbonyl asparagine (0.23 g), DEC (0.19 g), 1-hydroxybenzotriazole (0.15 g), N-methylmorpholine (0.1 g) and 2 ml anhydrous DMF. Stir 12 hours and evaporate solvent. Triturate the residue with water (10 ml) and collect the product by filtration. Wash with diethylether (3×20 ml) to obtain the title compound. R$_f$ (silica gel; CH$_2$Cl$_2$:CH$_3$OH, 95:5)=0.60.

G. Seryl-Asparaginyl-Valyl-(3,3-Diphenyl)Alanyl-Alanine Benzyl Ester Hydrochloride Add 6M HCl in dioxane (10 ml) to the product of Part F (0.75 q). Stir 10 minutes and evaporate excess acid and solvent. Add to this residue N-α-t-butyloxycarbonyl serine (0.2 g), DEC (0.19 g), 1-hydroxybenzotriazole (0.15 g), N-methylmorpholine (0.1 g), and 2 ml anhydrous DMF. Stir 12 hours and evaporate solvent. Triturate the residue with water (10 ml) and collect the product by filtration. Wash with diethyl ether (3×20 ml) and dry the product in vacuo. Add 6M HCl in dioxane (10 ml), stir 10 minutes, and evaporate the solvent. Purify on reverse phase HPLC (C-18 column; CH$_3$CN:H$_2$O:CF$_3$COOH, 399:599:2). Add 1N acueous HCl (10 ml) and evaporate the solvent in vacuo to obtain the title compound. FAB mass spec:(M+1)/e=703 (M-Cl).

Using the methods described in Example 1, the following compounds may be prepared:

Substitute phenylalanine for 3,3-diphenyl alanine to prepare seryl-asparaginyl-valyl-phenylalanyl-alanine benzyl ester, hydrochloride. FAB mass spec: (M+1)/e=627 (M-Cl).

Substitute 1-bromomethylnaphthylene for diphenylbromomethane to prepare seryl-asparaginyl-valyl-3-(1'-naphthyl)alanyl-alanine benzyl ester, hydrochloride. FAB mass spec: (M+1)/e=677 (M-Cl).

Substitute 2-bromomethylnaphthylene for diphenylbromomethane to prepare seryl-asparaginyl-valyl-3-(2'-naphthyl)alanyl-alanine benzyl ester hydrochloride. FAB mass spec: (M+1)/e=677 (M-Cl).

Substitute tryptophane for 3,3-diphenylalanine to prepare seryl-asparaginyl-valyl-tryptohanyl-alanine benzyl ester, hydrochloride. FAB mass spec: (M+1)/e=666 (M-Cl).

Substitute 1-bromomethyl-4-phenylbenzene for diphenylbromomethane to prepare seryl-asparaqinyl-valyl-3-(4-biphenyl)-alanyl-alanine benzyl ester, hydrochloride. FAB mass spec: (M+1)/e=703 (M-Cl).

Substitute cyclohexylmethylbromide for diphenylbromomethane to prepare seryl-asparaginyl-valyl-β-cyclohexylalanyl-alanine benzyl ester, hydrochloride. FAB mass spec: (M+1)/e=633 (M-Cl).

Substitute 3-iodo-L-tyrosine or 3,5-diiodo-L-tyrosine for 3,3-diphenylalanine to prepare serylasparaginyl-valyl-(3-iodo or 3,5-diiodo-L-tyrosinyl)-alanine benzyl ester, hydrochloride. Monoiodo FAB mass spec: (M+1)/e=769 (M-HCl); diiodo FAB mass spec: (M+1)=895 (M-Cl).

EXAMPLE 2

Seryl-Asparaginyl-Valyl-(3,3-Diphenyl)Alanyl-alanine Benzyl Amide, Hydrochloride

A. N-α-t-Butyloxycarbonyl-Alanine Benzyl Amide

Dissolve N-α-t-butyloxycarbonyl alanine (1.89 g), benzylamine (1.07 g), DEC (1.91 g) and 1-hydroxybenzotriazole hydrate (1.53 g) in 40 ml of CH$_2$Cl$_2$. Wash successively with saturated aqueous NaHCO$_3$, 10% citric acid, and water. Dry the organic layer over MgSO$_4$, filter, and evaporate to give the title compound. R$_f$(silica gel; CH$_2$Cl$_2$:CH$_3$OH, 98:2)=0.60.

B. Alanine Benzylamide, Hydrochloride

Dissolve the product of part A (0.5 g) in 6M HCl in dioxane (10 ml) stir 10 minutes and evaporate the solvent to obtain the title compound.

C. Substituting alanine benzylamide for 3,3-diphenylalanine, continue with the procedure described in Example 1, parts C-G to obtain the title compound.

The compounds of this invention are useful in view of their pharmacological properties. In particular, compounds of this invention possess activity as antihypertensive agents, as evidenced by their ability to reduce blood pressure in mammals in which the blood pressure has become abnormally elevated.

The compounds of this invention can be combined with pharmaceutical carriers to prepare well-known pharmaceutical forms suitable for parenteral administration. Such pharmaceutical compositions are useful in the treatment of cardiovascular disorders and particularly mammalian hypertension.

The effective daily antihypertensive dose (ED$_{50}$) of the compounds of this invention will typically be in the range of about 1 to about 100, preferably about 10 to about 100 mg/kg of mammalian weight, administered in a single or divided doses. The exact dose to be administered is determined by the attending clinician and is dependent upon where the particular compound lies within the above quoted range, as well as upon the age, weight and condition of the individual.

Generally, in treating humans having hypertension, the compounds of this invention may be administered to patients in need of such treatment in a dosage range of about 10 to about 500 mg per patient generally given several times a day, thus giving a total daily dose of from about 10 to about 2000 mg per day.

The compositions of the present invention are most preferably administered parenterally. Typical injectable formulations include solutions and suspensions. Also contemplated are mechanical delivery systems, e.g. transdermal dosace forms.

Following is an example of an injectable solution:

EXAMPLE 3

| Injectable Solution | mg/ml |
| --- | --- |
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad | 1.0 ml |

Dissolve the p-hydroxybenzoates in a portion of water for injection at 60°-70° C. and cool the solution to 25°-25° C. Charge and dissolve all other excipients and the active ingredient. Bring the solution to final volume, filter it through a sterilizing membrane and fill into sterile containers.

We claim:

1. A compound represented by the formula

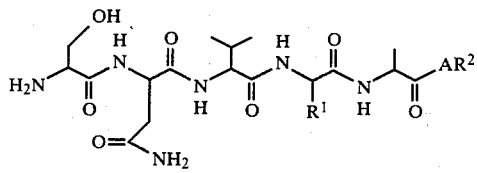

wherein

A is —O— or —NH—;

$R^1$ is arylmethyl wherein aryl is 1 or 2 phenyl rings, a polycyclic phenyl fused ring system having 10-14 carbon atoms, or a polycyclic phenyl ring system having two or more phenyl rings bonded to each other by ring carbons, a polycyclic phenyl ring system having two or more phenyl rings bonded to an alkyl group; substituted arylmethyl wherein aryl is as defined above and wherein the substituents on the aryl group are 1-3 substituents selected from hydroxy, halogen, lower alkyl, lower alkoxy, cycloalkyl or aryl; cycloalkylmethyl; substituted cycloalkylmethyl wherein the substituents on the cycloalkyl group are as defined for arylmethyl; hereroarylmethyl wherein heteroaryl is a monocyclic or bicyclic fused ring system comprising 5-10 atoms wherein 1 or more ring atoms are independently selected from nitrogen, oxygen or sulfur; or substituted heteroarylmethyl wherein heteroaryl is as defined above and wherein the substituents on the heteroaryl group are as defined for arylmethyl;

$R^2$ arylmethyl wherein aryl is as defined above in $R^1$; cycloalkylmethyl; substituted arylmethyl wherein aryl is as defined above in $R^1$; and substituted cycloalkylmethyl wherein the substituents are as defined in $R^1$ for arylmethyl; and the pharmaceutically acceptable salts thereof.

2. A compound of claim 1 wherein A is —O—.
3. A compound of claim 1 wherein A is —NH—.
4. A compound of claim 1 wherein $R^2$ is benzyl.
5. A compound of claim 1 wherein $R^1$ is represented by the formula

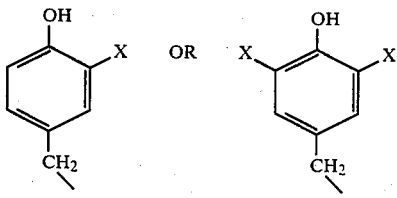

wherein X is chlorine, bromine or iodine

6. A compound of claim 1 wherein $R^1$ is selected from 1-naphthylmethyl, 2-naphthylmethyl, 4-phenylbenzyl, diphenylmethyl and 9-anthracenylmethyl.
7. A compound of claim 5 wherein $R^2$ is benzyl.
8. A compound of claim 7 wherein A is —O—.
9. A compound of claim 7 wherein A is —NH—.
10. A compound of claim 8 wherein X is iodine.
11. A compound of claim 9 wherein X is iodine.
12. A compound of claim 6 wherein $R^2$ is benzyl.
13. A compound of claim 12 wherein A is —O—.
14. A compound of claim 12 wherein A is —NH—.
15. A method of treating hypertension in mammals comprising administering to a hypertensive mammal an anti-hypertensive-effective amount of a compound of claim 1.
16. An anti-hypertensive pharmaceutical composition comprising an antihypertensive-effective amount of a compound of claim 1 in combination with a pharmaceutically acceptable carrier.

* * * * *